(12) United States Patent
Cho

(10) Patent No.: US 8,865,644 B2
(45) Date of Patent: Oct. 21, 2014

(54) RAPAMYCIN FORMULATION USING RECOMBINANT HIGH-DENSITY LIPOPROTEIN INCLUDING APOLIPOPROTEIN A-I AND A MUTANT THEREOF

(75) Inventor: Kyung-Hyun Cho, Daegu (KR)

(73) Assignee: Industry-Academic Cooperation Foundation, Yeungnam University, Gyeongsan-si, Gyeongsandbuk-do (KR)

( * ) Notice: Subject to any disclaimer, the term of this patent is extended or adjusted under 35 U.S.C. 154(b) by 0 days.

(21) Appl. No.: 13/881,857

(22) PCT Filed: Oct. 25, 2011

(86) PCT No.: PCT/KR2011/007966
§ 371 (c)(1),
(2), (4) Date: Jun. 11, 2013

(87) PCT Pub. No.: WO2012/057492
PCT Pub. Date: May 3, 2012

(65) Prior Publication Data
US 2013/0252879 A1    Sep. 26, 2013

(30) Foreign Application Priority Data
Oct. 26, 2010  (KR) .................. 10-2010-0104942

(51) Int. Cl.
*A61K 38/17* (2006.01)
*A61K 31/439* (2006.01)
*A61K 9/127* (2006.01)
*C07K 14/775* (2006.01)
*A61K 31/436* (2006.01)

(52) U.S. Cl.
CPC ........... *A61K 38/1709* (2013.01); *A61K 31/439* (2013.01); *A61K 9/1275* (2013.01); *C07K 14/775* (2013.01); *A61K 31/436* (2013.01)
USPC ........................................... 514/1.9; 514/7.4

(58) Field of Classification Search
CPC ............ A61K 38/1709; A61K 38/439; A61K 31/436; A61K 9/1275; A61K 9/1277; A61K 31/439; C07K 14/775
See application file for complete search history.

(56) References Cited

U.S. PATENT DOCUMENTS

| | | |
|---|---|---|
| 5,100,883 A | 3/1992 | Schiehser |
| 5,118,678 A | 6/1992 | Kao et al. |
| 5,120,725 A | 6/1992 | Kao et al. |
| 5,120,727 A | 6/1992 | Kao et al. |
| 5,120,842 A | 6/1992 | Failli et al. |
| 5,151,413 A | 9/1992 | Caufield et al. |
| 5,258,389 A | 11/1993 | Goulet et al. |
| 5,260,300 A | 11/1993 | Hu |
| 5,457,111 A | 10/1995 | Luly et al. |
| 5,527,907 A | 6/1996 | Or et al. |
| 5,536,729 A | 7/1996 | Waranis et al. |
| 5,583,139 A | 12/1996 | Or et al. |
| 5,672,605 A | 9/1997 | Or et al. |
| 5,935,995 A | 8/1999 | Bosslet et al. |
| 5,955,100 A | 9/1999 | Bosslet et al. |
| 6,146,658 A | 11/2000 | Bosslet et al. |
| 2005/0175666 A1 | 8/2005 | Ding |
| 2005/0287636 A1 | 12/2005 | Cho |

FOREIGN PATENT DOCUMENTS

| | | |
|---|---|---|
| JP | 2007-517550 A | 7/2007 |
| KR | 10-0452004 B1 | 9/2005 |
| KR | 10-2005-0122729 A | 12/2005 |
| WO | WO 92/05179 | 4/1992 |

OTHER PUBLICATIONS

Oda et al. (J. Lipid Res. 2006. 47:260-267).*
Park et al. (Human Gene Therapy. May 2010. 21:579-587).*
Rouf et al. (J. Liposome Res. 2009;19(4):322-31).*
Cho et al. (Eur J. clin Invest 2006;36 (12):875-882).*
International Search Report for PCT/KR2011/007966 mailed May 22, 2012 from Korean Intellectual Property Office.
Han,J,-M.,et al., Structural and Functional properties of V156K and A158E mutants of apolipoprotein A-I in the lipid-free . . . , Journal of Lipid Research,2005,vol. 46,pp. 586-596.
Morrisett, J.D. et al., Effects of sirolimus on plasma lipids, lipoprotein levels, and fatty acid . . . , Journal of Lipid Research, 2002, vol. 43, pp. 1170-1180.

* cited by examiner

*Primary Examiner* — James H Alstrum Acevedo
*Assistant Examiner* — Tara Martinez
(74) *Attorney, Agent, or Firm* — Sherr & Jiang PLLC

(57) ABSTRACT

Provided is a rapamycin formulation using a recombinant high-density lipoprotein including apolipoprotein mutant, the rapamycin formulation in which solubility of rapamycin and medical use, such as aging suppression and arteriosclerosis suppression, are improved by using recombinant high-density lipoprotein including apolipoprotein A-I and its mutant V156K.

2 Claims, 4 Drawing Sheets

CETP inhibition assay

Senescence associated-β-gal staining a : WT-rHDL          d : V156K-rapa-rHDL
b : V156K-rHDL       e : rapamycin in ethanol
c : WT-rapa-rHDL     f : 100% ethanol

RAPAMYCIN FORMULATION USING RECOMBINANT HIGH-DENSITY LIPOPROTEIN INCLUDING APOLIPOPROTEIN A-I AND A MUTANT THEREOF

CROSS REFERENCE TO PRIOR APPLICATION

This application is a National Stage Patent Application of PCT International Patent Application No. PCT/KR2011/007966 (filed on Oct. 25, 2011) under 35 U.S.C. §371, which claims priority to Korean Patent Application No. 10-2010-0104942 (filed on Oct. 26, 2010), which are all hereby incorporated by reference in their entirety.

TECHNICAL FIELD

The present invention relates to a rapamycin formulation that includes recombinant high-density lipoprotein including apolipoprotein A-I and its mutant V156K to improve solubility of rapamycin and medical use, such as aging suppression and arteriosclerosis suppression.

BACKGROUND ART a chemical formula of $C_{51}H_{79}NO_{13}$, and in solution, forms a structural trans-isomer and cis-isomer at a ratio of 4:1 (in chloroform solution) due to steric hindrance in vicinity of pipecolate amide bond. Rapamycin is hardly dissolved in water, aliphatic hydrocarbon, and diethylether, but is dissolved in alcohol, halogenated hydrocarbon, and dimethylsulfoxide. Rapamycin in a solution state is unstable in plasma and in a low-pH and neutral-pH buffer solution, at a temperature of 37° C., and decomposes with a half lifetime of less than 10 hours.

In particular, rapamycin has various bioactivities, such as an antifungal activity, an anti-cancer activity, and an immunosuppressive activity, and furthermore, it has been reported as a lifespan prolongation drug. Also, rapamycin is used as a coating agent for medical devices, such as a stent.

However, rapamycin has low bioavailability and solubility. To overcome such disadvantages, many rapamycin derivatives have been synthesized: carboxylic acid esters (PCT WO 92/05179), carbamates (U.S. Pat. No. 5,118,678), carbonate (U.S. Pat. No. 5,260,300), amide ester (U.S. Pat. No. 5,118, 678), fluorinated esters (U.S. Pat. No. 5,100,883), acetal (U.S. Pat. No. 5,151,413), silyl ethers (U.S. Pat. No. 5,120, 842), bicyclic derivatives (U.S. Pat. No. 5,120,725), rapamycin dimers (U.S. Pat. No. 5,120,727), and O-aryl, O-alkyl, O-alkenyl, and O-alkynyl derivatives (U.S. Pat. No. 5,258, 389), and various rapamycin drug precursors (U.S. Pat. No. 5,672,605, U.S. Pat. No. 5,583,139, U.S. Pat. No. 5,527,907, U.S. Pat. No. 5,457,111, U.S. Pat. No. 5,955,100, U.S. Pat. No. 6,146,658, and U.S. Pat. No. 5,935,995).

However, there is still a limit on the development of a drug with improved bioavailability based on an increase in solubility of rapamycin. Accordingly, the development of a drug that improves the solubility of rapamycin is needed.

DETAILED DESCRIPTION OF THE INVENTION

Technical Problem

The inventors of the present invention studied for the improvement of the solubility of rapamycin and found that when rapamycin is capsulated by using recombinant high-density lipoprotein including apolipoprotein mutant V156K, the solubility of rapamycin is improved and a medical use, such as aging suppression and arteriosclerosis suppression, is improved, thereby completing the present invention.

The present invention provides a novel rapamycin formulation for the improvement of the solubility of rapamycin and a medical use, such as aging suppression and arteriosclerosis suppression, and a method of preparing the same.

Technical Solution

A rapamycin formulation according to an embodiment of the present invention includes rapamycin in an amount of 0.1 to 10 parts by weight based on a total weight of 100 parts by weight of a recombinant high-density lipoprotein, wherein the recombinant high-density lipoprotein includes apolipoprotein mutant V156K that is prepared by substituting an amino acid at the location of No. 156 of apolipoprotein (apoA-I) with lysine.

Advantageous Effects

A rapamycin formulation according to the present invention is prepared by capsulating rapamycin using recombinant high-density lipoprotein including apolipoprotein mutant V156K. Due to the capsulation, the solubility of rapamycin with low solubility and bioavailability are improved, and aging suppression and arteriosclerosis suppression thereof are also improved.

BEST MODE

Figure 1:
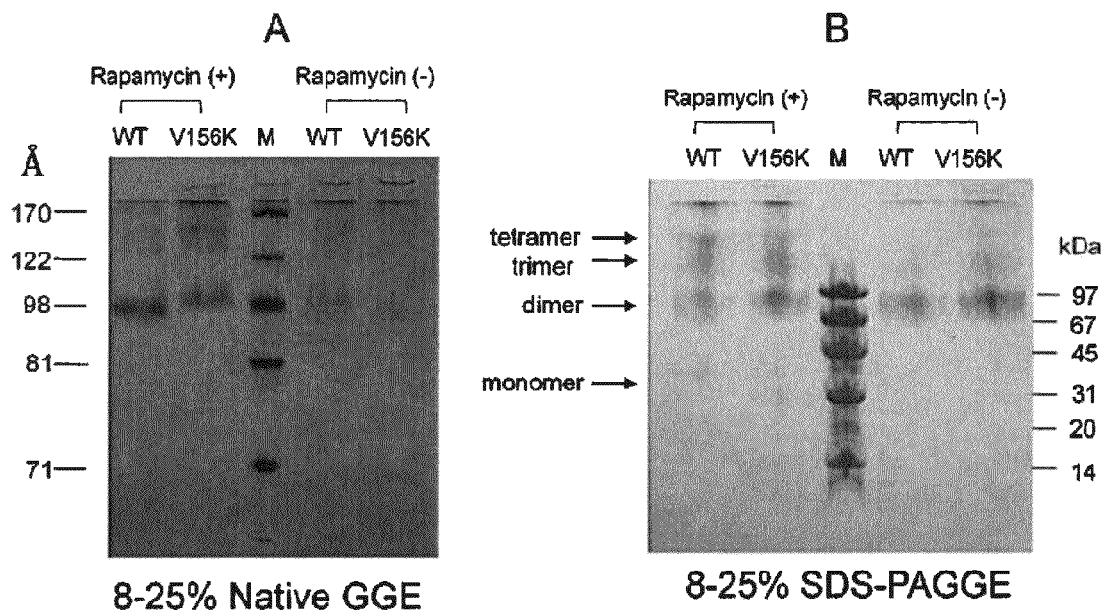
FIG. 1A shows electrophoresis results of recombinant high-density lipoprotein in a native state.
FIG. 1B shows the number of apoA-I molecules in recombinant high-density lipoprotein particles.

A rapamycin formulation according to an embodiment of the present invention includes rapamycin in an amount of 0.1 to 10 parts by weight based on a total 100 parts by weight of a recombinant high-density lipoprotein, wherein the recombinant high-density lipoprotein includes apolipoprotein mutant V156K that is prepared by substituting an amino acid at the location of No. 156 of apolipoprotein (apoA-I) with lysine.

In this regard, when the amount of rapamycin is outside the upper limit so that the rapamycin is excessively included in the rapamycin formulation, solubility thereof may be low and rapamycin may precipitate. However, when rapamycin is included in a very small amount, the rapamycin content may lack and rapamycin effects may be low.

The recombinant high-density lipoprotein may include apolipoprotein mutant V156K, phospholipid, cholesterol, and sodium cholate, at a mole ratio of 90 to 100 of apolipoprotein mutant V156K: 1 to 10 of phospholipid: 0.1 to 2.0 of cholesterol: 120 to 180 of sodium cholate.

In this regard, when the amount of apolipoprotein mutant V156K is outside this amount range, protein may precipitate, and when the amounts of the phospholipid and cholesterol are outside these ranges, high-density lipoprotein formation disorders may occur, and when the amount of sodium cholate is outside this range, lipoprotein formation disorders may occur.

The amount of the rapamycin may be in a range of 0.1 to 20 parts by weight based on a total 100 parts by weight of apolipoprotein mutant V156K. In this regard, when rapamycin is outside the upper limit and is excessively included, protein precipitation and lipoprotein formation disorders may occur, and when the amount of rapamycin is small, the rapamycin content may lack and rapamycin effects may decrease.

The rapamycin formulation according to an embodiment of the present invention contributes to an increase in solubility of Rapamycin that has low solubility and bioavailability. In particular, the rapamycin formulation according to an embodiment of the present invention contributes to an improvement in aging suppression and arteriosclerosis suppression effects of rapamycin.

The rapamycin formulation may be prepared as an oral administration formulation, for example, tabulate, troches, lozenge, aqueous or oil suspension, prepared powder or granule, emulsion, hard or soft capsule, syrup, or elixirs. For the preparation as tablet and capsule formulations, a binder, such as lactose, sacarose, sorbitol, manitol, starch, amilopectin, cellulose, or gelatin; an excipient, such as dicalcium phosphate; a disintegrant, such as corn powder or sweet potato powder; and a lubricant, such as magnesium stearate, calcium stearate, sodium stearylfumarate, or polyethyleneglycol wax, may be used. A capsule formulation may further include, in addition to these materials, a liquid carrier, such as fatty oil.

Also, the rapamycin formulation may be non-orally administered. The non-oral administration may be an intravenous, intraarteria, intramuscular, transdermal, intrapulmonary, subcutaneous, intradermal, or intraepidural administration performed via cheek, anus, vagina, conjunctiva, or intranasal tissues, or the non-oral administration may be performed by inoculation or transplantation into, for example, cancer tissues. A non-oral administration formulation may be prepared as follows: a recombinant high-density lipoprotein is mixed with a stabilizer or buffer in water to prepare a solution or a suspension, and then, the mixture is prepared in an ample unit or a vial unit.

Also, a dosage of the rapamycin formulation for medical use, such as aging suppression or arteriosclerosis suppression, may be, in general, and may be in a range of 15 to 45 mg/day, or 45 to 80 mg/based on 1 kg of adult patient weight, and based on the determination of a physician or pharmacist, the dosage may be administered once or several times, or 2 to 3 times per day, at predetermined time intervals.

Also, the present invention provides a method of preparing a rapamycin formulation, wherein the method includes: preparing apolipoprotein mutant V156K that is prepared by substituting an amino acid at the location of No. 156 of apolipoprotein (apoA-I) with lysine; mixing the apolipoprotein mutant V156K with phospholipid, cholesterol, and sodium cholate to prepare recombinant high-density lipoprotein; and adding rapamycin to the recombinant high-density lipoprotein.

Mode of the Invention

Hereinafter, embodiments of the present invention are described in detail by referring to Examples below. Examples presented herein are provided for illustrative purpose only.

Example 1

Preparation of Recombinant HDL (rHDL) Containing Rapamycin

1. Preparation of WT apoA-I And V156K-apoA-I

WT apoAd (SEQID NO: 1) and V156K-apoA-I (SEQID NO: 2) were expressed in *E. coli* expression system using pET30a(+) expression vector and BL21(DE3) host. Thereafter, the result was purified by $Ni^{2+}$-column chromatography according to a known method (*European Journal of Clinical Investigation*, 36: 875-882, 2006) until a purity level reached at least 95% or more.

2. Preparation of Rapamycin-Containing rHDL

Rapamycin-containing recombinant high-density lipoprotein (rHDL) was prepared using sodium cholate dialysis (*J Lipid Res*, 46: 589-596, 2005). In this regard, an initial molar ratio of pamitoyloleoyl phosphatidylcholine (POPC): cholesterol: apoA-I of any one of WT apoA-I and V156K-apoA-I: sodium cholate was 95:5:1:150. Various concentrations of rapamycin was dissolved in the rHDL so that it was identified that the solubility of rapamycin was optimized when 0.1 mg of rapamycin and 1 mg of apoA-I were included in 1 ml of rHDL.

0.09 mg/ml of rapamycin was dissolved well in rHDL including any one of WT and V156K (1 mg/ml of protein).

3. Characteristics of Rapamycin-Containing rHDL

A particle distribution was identified using 8-25% polyacrylamide gradient gel electrophoresis (PAGGE, Pharmacia Phast system) according to the prior paper prepared by the same inventors (*J Lipid Res*, 46: 589-596, 2005), and was compared with reference global protein.

As a result, as illustrated in FIG. 1, a major band of rapamycin-containing V156K-rHDL indicates a particle size of about 101 Å, which is slightly larger than rapamycin-containing WT-rHDL (WT-rapa-rHDL) having a particle size of 98 Å. Also, rapamycin-free V156K-rHDL had a particle size of about 99 Å. Also, compared to WT-rapa-rHDL, V156K-rHDL showed a large band indicating a particle size of about 140 Å. Accordingly, it was confirmed that V156K-rHDL had a better ability for the capsulation of rapamycin.

The number of apoA-I molecules per rHDL particle in the presence of rapamycin was analyzed using cross-linking with bis-sulfosuccinimidyl suberate (BS3) (*J Lipid Res*, 46: 589-596, 2005). In this regard, a reaction product produced by cross-linking with BS3 was analyzed on 8-25% gradient gel by SDS-PAGE.

As a result, for the rapamycin-containing rHDL, each particle included four apoA-I molecules, and for the rapamycin-free rHDL, each particle included two or three apoA-I molecules. From this result, it was confirmed that more apoA-I molecules are required to dissolve rapamycin.

Example 2

Anti-Oxidative Activity Examination

1. Iron Ion Reductive Abilit Examination

Iron ion reductive ability of plasma (FRAP) was determined using a method disclosed by Benzie and Strain (Anal Biochem, 239: 70-6, 1996). That is, FRAP reagent was prepared by mixing 25 mL of 0.2M acetate buffer (pH 3.6), 2.5 mL of 10 mM 2,4,6-tripyridyl-s-triazine (TPTZ) and 2.5 mL of 20 mM $FeCl_3.6H_2O$. An anti-oxidative activity of rHDL was determined by measuring an increase in absorption resulting from a generated bi-valent iron ion. The prepared FRAP reagent (300 µl) was mixed with the same amount of diluted rHDL (2 mg/ml, 10 µl), and then, an absorption thereof was measured by using DU800 spectrometer (Beckman Coulter) at a temperature of 25° C. at intervals of 10 minutes every 20 seconds at a wavelength of 593 nm. In this regard, the used DU800 spectrometer included MultiTemp III thermocirculator.

Figure 2:
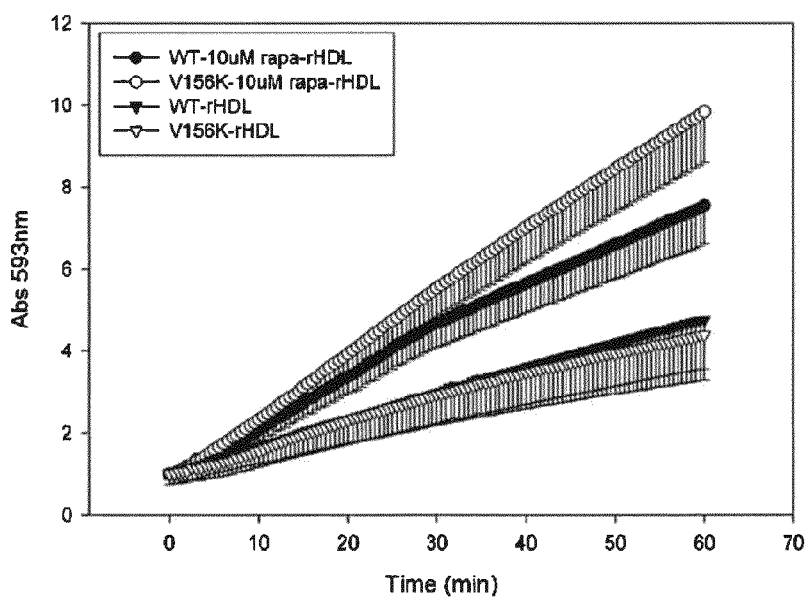
FIG. 2 shows reductive effects of a rapamycin formulation according to an embodiment of the present invention.

As a result, as illustrated in FIG. 2, an anti-oxidative activity of the rapamycin-free V156K-rHDL and WT-rHDL was increased four-fold, and an iron ion reductive ability of V156K-rapa-rHDL and WT-rapa-rHDL was increased ten- and six-fold, respectively.

2. Copper-Mediated LDL Oxidation Suppression Activity Examination

An anti-oxidative activity with respect to copper-mediated LDL oxidation was examined as follows: 300 µg of LDL was reacted with the respective rapamycin-containing rHDL (final concentration, 10 µ/ml) in the presence of 10 µM $CuSO_4$ for 2 hours. During the reaction, an amount of the formed conjugated diene was measured by using a DU800 spectrometer at a temperature of 24.5° C. and an absorption wavelength of 234 nm. In this regard, the used DU800 spectrometer included MultiTemp III thermocirculator. A conjugated diene level was expressed as a ratio of $A_{234}$ to $A_{280}$, which were measured in consideration of a molecular absorption coefficient (apoA-I $\epsilon_{280}=1.13M^{-1} cm^{-1}$) by using a spectrometer.

Figure 3:
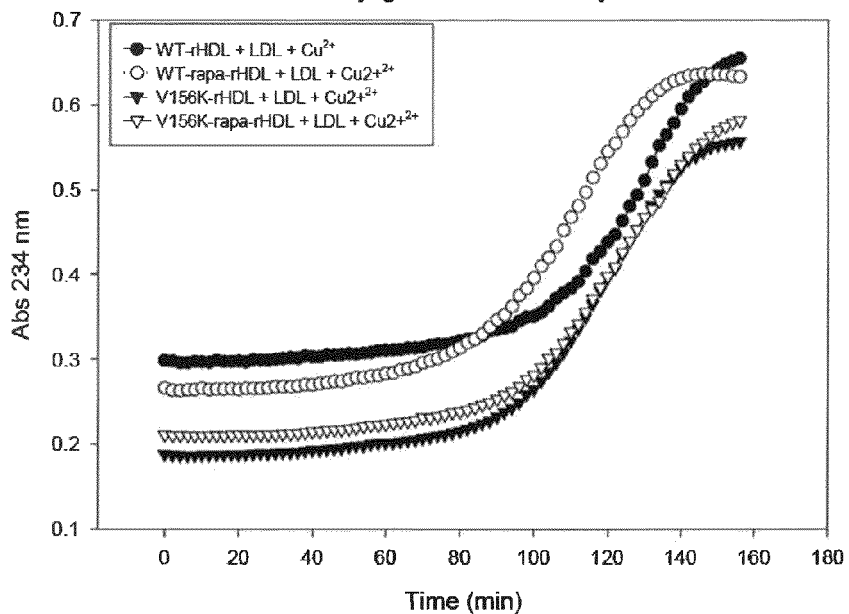
FIG. 3 is a graph showing LDL anti-oxidative effects of a rapamycin formulation according to an embodiment of the present invention.

As a result, as illustrated in FIG. 3, up to the reaction time of 80 minutes, all rHDL showed excellent oxidation suppression activity, and up to the reaction time of 150 minutes, regardless of the presence or absence of rapamycin, V156K-rHDL showed better oxidation suppression activity than WT-rHDL.

Figure 4:
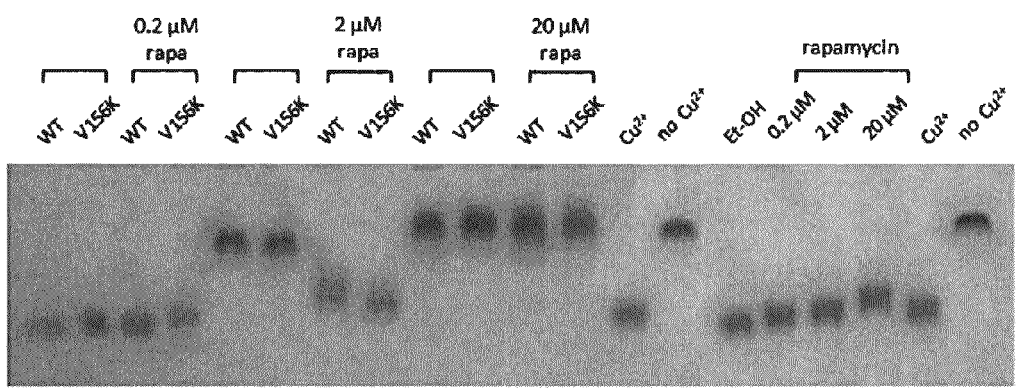
FIG. 4 shows agarose electrophoresis results showing LDL anti-oxidative effects of a rapamycin formulation according to an embodiment of the present invention.

After the reaction, oxidative levels of LDL were compared by performing agarose gel electrophoresis. As a result, as illustrated in FIG. 4, depending on concentration, LDL treated with rHDL showed low mobility and thus excellent anti-oxidative effects. From among those, anti-oxidative effects of V156K-rapa-rHDL were increased. Even at the same concentration, when dissolved in rHDL, better anti-oxidative effects were obtained than when treated with only rapamycin.

Example 3

Cholesteryl Ester Transfer Protein (CETP) Analysis apoA-I-containing rHDL and cholesteryl oleate were synthesized by using a trace amount of $[^3H]$-cholesteryl oleate (TRK886, 3.5 µCi/mg of apoA-I; GE Healthcare) according to a method disclosed by Cho et al. (Biochim Biophys Acta, 1391: 133-44, 1998). To promote separation from a CE-receptor, rHDL was fixed by using CNBr-activated Sepharose 4B resin (Amersham Biosciences). A CE-transfer reaction was performed in 300 µl of a reaction mixture. The reaction mixture contained a radioactive isotope-labeled $[^3H]$-CE-rHDL-agarose (0.05 ml) as a source for cholesteryl ester transfer protein (CETP)-donor and human LDL (0.05 µl, 0.25 mg/mL) as a source for cholesteryl(CE)-receptor. After reaction at a temperature of 37° C., the reaction product was centrifuged (10,000 g) at a temperature of 4° C. for 3 minutes to stop the reaction. A supernatant (150 µl) was subjected to scintillation counting to calculate a percentage of $[^3H]$-CE transferred from rHDL to LDL.

Figure 5:
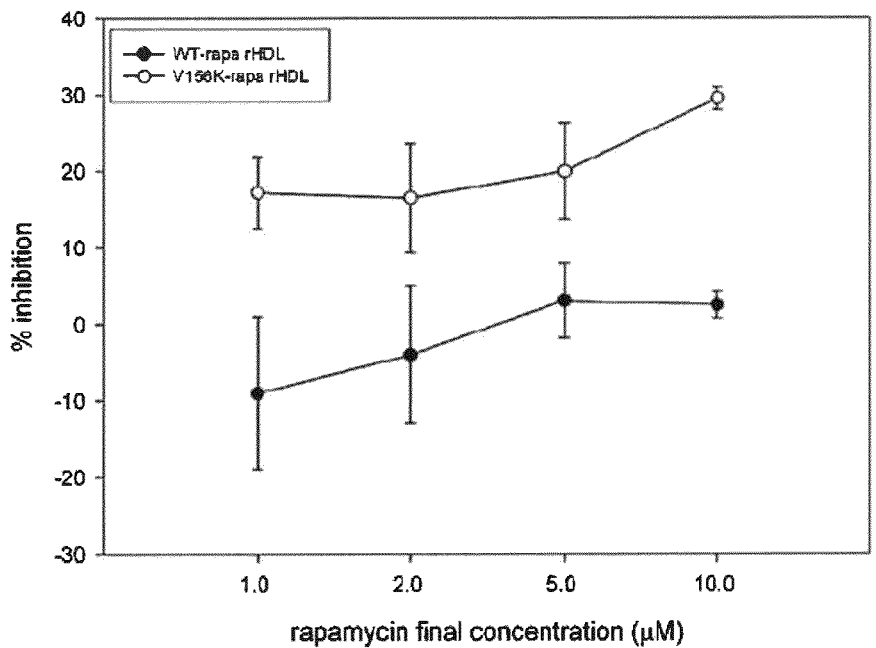
FIG. 5 shows CETP suppression effects of a rapamycin formulation according to an embodiment of the present invention.

As a result, as illustrated in FIG. 5, rapamycin itself did not show an appropriate CETP suppression activity, and V156K-rapa-rHDL (3.5 µM protein) showed 29% CETP suppression activity at 10 µM rapamycin and WT-rapa-rHDL (3.5 µM protein) did not show an appropriate CETP suppression activity.

Example 4

Cell Aging Suppression Analysis

Primary human dermal fibroblast (HDFs) was cultured in a 5% $CO_2$-humidified incubator by using Dulbecco's modified Eagle's Medium (DMEM) medium at a concentration of $1 \times 10^5$ cells on 100 mm culture dish. When sub-cultured 80 to 90% confluently, the cells were treated with trypsin, and a population doubling (PD) number was monitored according to the prior literature of the same inventors (*J. Gerontol. A. Biol. Sci. Med. Sci.* 2010; 65 (6): 600-610). For experiments, 6-passaged cells (PD<24) were sub-cultured to prepare a sufficient number of cells.

Aging levels were evaluated by comparing cell aging-associated galactosidase (SA-β-gal) activity according to a known method (Proc Natl Acad Sci USA 92 (1995) 9363-9367). That is, cells were fixed in 3% paraformaldehyde dissolved in PBS for 5 minutes, washed three times with PBS, and cultured in a SA-β-gal staining solution (40 mM citric acid/phosphate [pH 6.0], 5 mM potassium ferrocyanide, 5 mM potassium ferricyanide, 150 mM NaCl, 2 mM $MgCl_2$, and 1 mg/mL 5-bromo-4-chloro-3-indolyl-X-galactosidase) at a temperature of 37° C. for 16 hours. Under phase-contrast microscope, a percentage point of aged cells stained with blue was calculated. After staining, the cell size was quantified from the number of randomly selected identical cells by using computer-assisted morphometer using Image Proplus software (version 4.5.1.22; Media Cybernetics, Bethesda, Md., USA).

Figure 6:
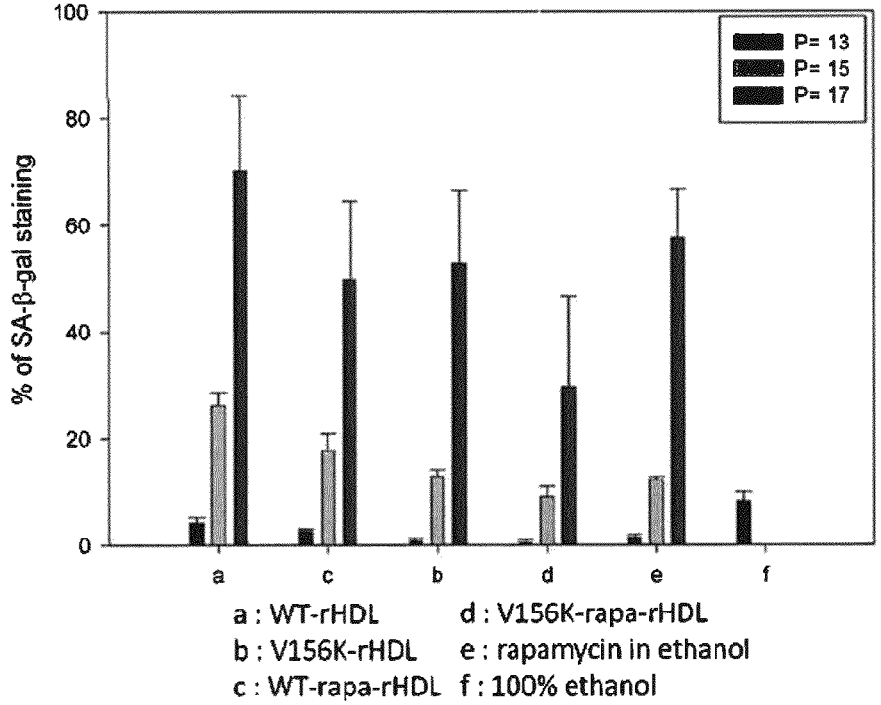
FIGS. 6 and 7 show anti-aging effects of a rapamycin formulation according to an embodiment of the present invention.
Figure 7:
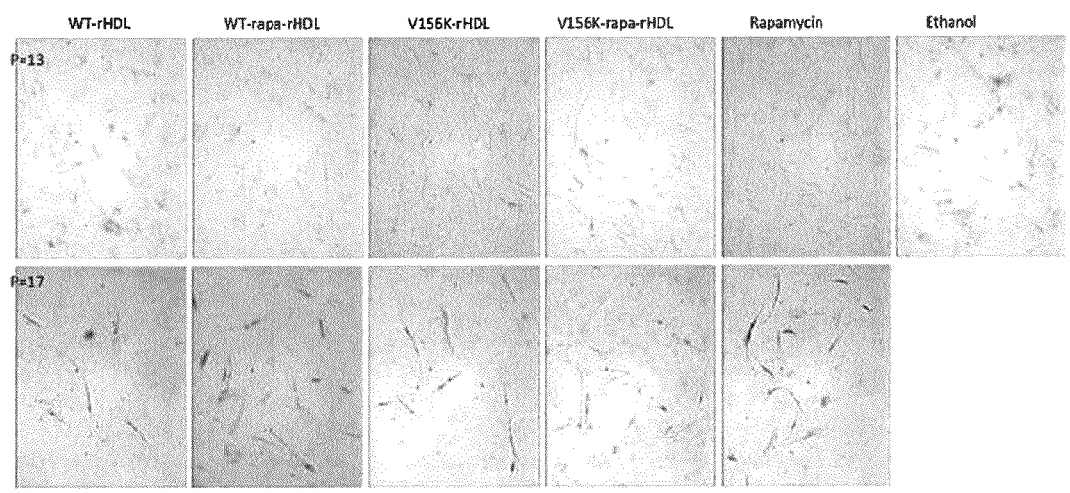

As a result, as illustrated in FIGS. 6 and 7, when compared with V156K-rHDL at the same passage number, WT-rHDL treated group showed more SA-β-gal positive cells. At passage 17, WT-rHDL and V156K-rHDL respectively showed 70% and 49% of SA-β-gal positive cells. However, in the presence of final 1 µM rapamycin, WT-rapa-rHDL and V156K-rapa-rHDL respectively showed 52% and 29% of stained cells. V156K-rapa-rHDL treated group showed a much smaller number of SA-β-gal stained cells than rapamycin alone treated group. Accordingly, synergetic anti-aging effects of V156K and rapamycin was able to be expected.

Sequence List Pretext

SEQ ID NO: 1 indicates an amino acid sequence of wild-type apoA-I,
SEQ ID NO: 2 indicates an amino acid sequence of V156K-apoA-I.

The invention claimed is:

1. A rapamycin formulation comprising rapamycin and a recombinant high-density lipoprotein; wherein the rapamycin is present in an amount of 0.1 to 10 parts by weight based on a total 100 parts by weight of the recombinant high-density lipoprotein comprising an apolipoprotein (apoA-I) mutant V156K; the recombinant high-density lipoprotein comprises a mole ratio of 90 to 100 of the apoA-I mutant V156K, 1 to 10 of phospholipid, 0.1 to 2.0 of cholesterol, and 120 to 180 of sodium cholate; wherein the apoA-I mutant V156K is prepared by substitution of the amino acid valine at residue 156 with the amino acid lysine.

2. A method of preparing a rapamycin and recombinant high-density lipoprotein formulation comprising: preparing an apoA-I mutant V156K by substituting the amino acid valine at residue 156 with lysine; mixing the apoA-I mutant V156K with a phospholipid, cholesterol, and sodium cholate to prepare the recombinant high-density lipoprotein; and adding rapamycin to the recombinant high-density lipoprotein.

* * * * *

```
                           SEQUENCE LISTING

<160> NUMBER OF SEQ ID NOS: 2

<210> SEQ ID NO 1
<211> LENGTH: 243
<212> TYPE: PRT
<213> ORGANISM: Homo sapiens

<400> SEQUENCE: 1

Asp Glu Pro Pro Gln Ser Pro Trp Asp Arg Val Lys Asp Leu Ala Thr
 1               5                  10                  15

Val Tyr Val Asp Val Leu Lys Asp Ser Gly Arg Asp Tyr Val Ser Gln
             20                  25                  30

Phe Glu Gly Ser Ala Leu Gly Lys Gln Leu Asn Leu Lys Leu Leu Asp
         35                  40                  45

Asn Trp Asp Ser Val Thr Ser Thr Phe Ser Lys Leu Arg Glu Gln Leu
     50                  55                  60

Gly Pro Val Thr Gln Glu Phe Trp Asp Asn Leu Glu Lys Glu Thr Glu
 65                  70                  75                  80

Gly Leu Arg Gln Glu Met Ser Lys Asp Leu Glu Glu Val Lys Ala Lys
                 85                  90                  95

Val Gln Pro Tyr Leu Asp Asp Phe Gln Lys Lys Trp Gln Glu Glu Met
            100                 105                 110

Glu Leu Tyr Arg Gln Lys Val Glu Pro Leu Arg Ala Glu Leu Gln Glu
        115                 120                 125

Gly Ala Arg Gln Lys Leu His Glu Leu Gln Glu Lys Leu Ser Pro Leu
    130                 135                 140

Gly Glu Glu Met Arg Asp Arg Ala Arg Ala His Val Asp Ala Leu Arg
145                 150                 155                 160

Thr His Leu Ala Pro Tyr Ser Asp Glu Leu Arg Gln Arg Leu Ala Ala
                165                 170                 175

Arg Leu Glu Ala Leu Lys Glu Asn Gly Gly Ala Arg Leu Ala Glu Tyr
            180                 185                 190

His Ala Lys Ala Thr Glu His Leu Ser Thr Leu Ser Glu Lys Ala Lys
        195                 200                 205

Pro Ala Leu Glu Asp Leu Arg Gln Gly Leu Leu Pro Val Leu Glu Ser
    210                 215                 220

Phe Lys Val Ser Phe Leu Ser Ala Leu Glu Glu Tyr Thr Lys Lys Leu
225                 230                 235                 240

Asn Thr Gln

<210> SEQ ID NO 2
<211> LENGTH: 243
<212> TYPE: PRT
<213> ORGANISM: Artificial Sequence
<220> FEATURE:
<223> OTHER INFORMATION: V156K-apoA-I

<400> SEQUENCE: 2

Asp Glu Pro Pro Gln Ser Pro Trp Asp Arg Val Lys Asp Leu Ala Thr
 1               5                  10                  15
```

```
Val Tyr Val Asp Val Leu Lys Asp Ser Gly Arg Asp Tyr Val Ser Gln
            20              25              30

Phe Glu Gly Ser Ala Leu Gly Lys Gln Leu Asn Leu Lys Leu Leu Asp
        35              40              45

Asn Trp Asp Ser Val Thr Ser Thr Phe Ser Lys Leu Arg Glu Gln Leu
    50              55              60

Gly Pro Val Thr Gln Glu Phe Trp Asp Asn Leu Glu Lys Glu Thr Glu
65              70              75              80

Gly Leu Arg Gln Glu Met Ser Lys Asp Leu Glu Glu Val Lys Ala Lys
                85              90              95

Val Gln Pro Tyr Leu Asp Asp Phe Gln Lys Lys Trp Gln Glu Glu Met
            100             105             110

Glu Leu Tyr Arg Gln Lys Val Glu Pro Leu Arg Ala Glu Leu Gln Glu
            115             120             125

Gly Ala Arg Gln Lys Leu His Glu Leu Gln Glu Lys Leu Ser Pro Leu
130             135             140

Gly Glu Glu Met Arg Asp Arg Ala Arg Ala His Lys Asp Ala Leu Arg
145             150             155             160

Thr His Leu Ala Pro Tyr Ser Asp Glu Leu Arg Gln Arg Leu Ala Ala
            165             170             175

Arg Leu Glu Ala Leu Lys Glu Asn Gly Gly Ala Arg Leu Ala Glu Tyr
            180             185             190

His Ala Lys Ala Thr Glu His Leu Ser Thr Leu Ser Glu Lys Ala Lys
            195             200             205

Pro Ala Leu Glu Asp Leu Arg Gln Gly Leu Leu Pro Val Leu Glu Ser
    210             215             220

Phe Lys Val Ser Phe Leu Ser Ala Leu Glu Glu Tyr Thr Lys Lys Leu
225             230             235             240

Asn Thr Gln
```